United States Patent
Damavarapu et al.

(10) Patent No.: US 9,440,936 B1
(45) Date of Patent: Sep. 13, 2016

(54) SYNTHESIS OF 3,4-BIS(4-NITRO-1,2,5-OXADIZAOL-3-YL)-1,2,5-OXADIZAOLE-N-OXIDE (DNTF) USING 3-CHLOROCARBOHYDROXYMOYL-4-NITRO-1,2,5-OXADIZAOLE

(71) Applicant: The United States of America, as Represented by the Secretary of the Army, Washington, DC (US)

(72) Inventors: Reddy S. Damavarapu, Hackettstown, NJ (US); Raja G. Duddu, Hackettstown, NJ (US); John H. Hoare, Hackettstown, NJ (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 15/060,928

(22) Filed: Mar. 4, 2016

Related U.S. Application Data

(60) Provisional application No. 62/131,972, filed on Mar. 12, 2015.

(51) Int. Cl.
*C07D 271/08* (2006.01)
*C07D 413/14* (2006.01)

(52) U.S. Cl.
CPC ........... *C07D 271/08* (2013.01); *C07D 413/14* (2013.01)

(58) Field of Classification Search
CPC .................................................. C07D 271/08
See application file for complete search history.

(56) References Cited

PUBLICATIONS

Tselinskii et al. Russian Journal of Organic Chemistry, 2001, 37, 1708-1712.*
Hua-Ping Ren et al, The [Bmim]4W10O23 Catalyzed Oxidation of 3,4-Diaminofurazan to 3,4-Dinitrofurazan in Hydrogen Peroxide, Industrial & Engineering Chemistry Research, 2011, pp. 6615-6619, 50, ACS Publications.
I.V. Tselinksii, Synthesis and Reactivity of Carbohydroximolyl Axides: 4-Substituted 1,2,5-Oxadiazole-3-carbohydroximoyl Azides and 1-Hydroxy-5-(4-R-1,2,5-oxadiazol-3-yl)tetrazoles, Russian Journal of Organic Chemistry, 2001, pp. 1707-1712, 37, Tselinskii, Mel'nikova, Romanova.
Zhao Feng-Qi et al., Thermochemical Properties and Non-isothermal Decomposition Reaction Kinetics of 3,4-dinitrofurazanfuroxan (DNTF), Journal of Hazardous Materials, 2004, pp. 67-71, A113, Elsevier.
Aleksei B. Sheremetev et al., Desilylative Nitration of C,N-Disilylated 3-Amino-4-Methylfurazan, J. Heterocyclic Chem., 2005, pp. 1237-1242, 42.
Choong Hwan Lim et al., Synthesis and Characterization of Bisnitrofurazanfuroxan, Bull. Korean Chem. Soc., 2010, pp. 1400-1402, 31, No, 5.

\* cited by examiner

*Primary Examiner* — Matthew Coughlin
(74) *Attorney, Agent, or Firm* — Lisa H. Wang

(57) ABSTRACT

A novel method for preparing 3-chlorocarbohydroxymoyl-4-nitro-1,2,5-oxadiazole by reacting 4-amino-3-chlorocarbohydroxymoyl-1,2,5-oxadiazole with $H_2O_2$ and a tungsten based catalyst and use of the prepared 3-chlorocarbohydroxymoyl-4-nitro-1,2,5-oxadiazole for synthesizing 3,4-Bis(4-nitro-1,2,5-oxadizaol-3-yl)-1,2,5-oxadiazole-N-oxide (DNTF).

4 Claims, No Drawings

SYNTHESIS OF 3,4-BIS(4-NITRO-1,2,5-OXADIZAOL-3-YL)-1,2,5-OXADIZAOLE-N-OXIDE (DNTF) USING 3-CHLOROCARBOHYDROXYMOYL-4-NITRO-1,2,5-OXADIZAOLE

CROSS REFERENCE TO RELATED APPLICATIONS

The present application is a non-provisional application that claims the benefit of the provisional patent application entitled "Synthesis Method for Preparation of 3,4-Bis(4-nitro-1,2,5-oxadizaol-3-yl)-1,2,5-oxadiazole-N-oxide (DNTF)" filed Mar. 12, 2015, as Ser. No. 62/131,972.

RIGHTS OF THE GOVERNMENT

The inventions described herein may be manufactured and used by or for the United States Government for government purposes without payment of any royalties.

FIELD OF INVENTION

A process for producing 3,4-Bis(4-nitro-1,2,5-oxadizaol-3-yl)-1,2,5-oxadiazole-N-oxide (DNTF), an energetic material, through a novel process for preparing its precursor 3-chlorocarbohydroxymoyl-4-nitro-1,2,5-oxadiazole.

BACKGROUND OF THE INVENTION

There has been significant research on the synthesis and development of new energetic materials to meet the needs of U.S. Department of Defense. It is in this context that research has focused on a promising melt-castable energetic material 3,4-Bis(4-nitro-1,2,5-oxadizaol-3-yl)-1,2,5-oxadiazole-N-oxide (DNTF). Synthetic methods for preparing DNTF mainly involve treating 4-amino-3-chlorocarbohydroxymoyl-1,2,5-oxadiazole (chloro oxime) (1) with a base followed by extractive work-up to produce 3,4-bis (aminofurazano) furoxan (furoxofurazane) (2). The resulting furoxofurazane is further oxidized to produce DNTF (4).

Alternative methods have been explored to prepare a DNTF precursor by reacting 4-amino-3-chlorocarbohydroxymoyl-1,2,5-oxadiazole (chloro oxime)(1) with NaNO2 and an acid to convert the amino group in chloro oxime (1) into the corresponding nitro group in, 3-chlorocarbohydroxymoyl-4-nitro-1,2,5-oxadiazole (3). These experiments, however, were unsuccessful. Thus, a need exists for preparing DNTF using alternative methods. Disclosed herein is a novel method for synthesizing 3-chlorocarbohydroxymoyl-4-nitro-1,2,5-oxadiazole, an intermediate useful for the preparation of DNTF.

SUMMARY OF THE INVENTION

A novel process for preparing 3-chlorocarbohydroxymoyl-4-nitro-1,2,5-oxadiazole, a precursor, using a tungsten catalyst and aqueous $H_2O_2$ and methods for synthesizing DNTF using such precursor.

DETAILED DESCRIPTION

A novel method for synthesis of 3-chlorocarbohydroxymoyl-4-nitro-1,2,5-oxadiazole (3) is disclosed herein. This compound is further reacted with K2CO3 to produce an alternative method for preparing the energetic material DNTF as discussed in further detail below.

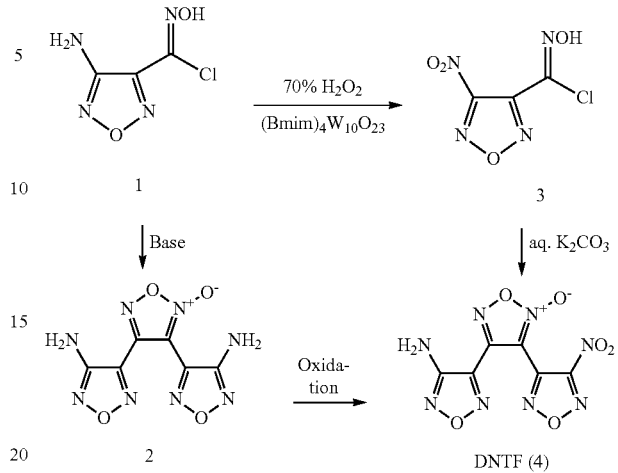

Schematic 1

Preparation of 3-chlorocarbohydroxymoyl-4-nitro-1,2,5-oxadiazole 3-chlorocarbohydroxymoyl-4-nitro-1,2,5-oxadiazole, compound 3, a precursor to DNTF is prepared according to the process illustrated in schematic 1. The amino group of compound 1 was subjected to oxidation using aq. 70% $H_2O_2$ in presence of a tungsten based catalyst initially at room temperature, followed by heating at 52° C. for 4 h. An extractive work-up followed by removal of solvent afforded a pale yellow liquid. Carbon NMR analysis of this liquid showed a resonance at 158.71 ppm, a triplet due to coupling of the nitro group nitrogen with ring carbon, suggesting the formation of the desired nitro compound 3.

The identity of the liquid, an ethereal solution, was characterized by reacting it with an aq. potassium carbonate ($K_2CO_3$) solution. After stirring the reaction mixture at room temperature for 2 h followed by an extractive workup and removal of solvent yielded crude DNTF. The crude DNTF was purified by triturating the crude with diethyl ether, and separation of the solid via filtration. The spectral and thermal data of the white solid thus obtained matched with that of the literature reported values.

Preparation of 3,4-Bis(4-nitro-1,2,5-oxadizaol-3-yl)-1,2,5-oxadiazole-N-oxide, (DNTF)

A heterogeneous mixture of 3-chlorocarbohydroximoyl-4-amino-1,2,5-oxadiazole (400 mg) in 70% $H_2O_2$ (10 mL) and $(Bmim)_4W_{10}O_{23}$ catalyst (200 mg) was stirred at room temperature for 16 h and then kept at 52° C. for 4 h. The reaction mixture was diluted with water (100 mL) and extracted with ethylacetate (3×30 mL). The combined organic layer was washed with water (2×50 mL), brine (1×50 mL), dried ($Na_2SO_4$) and filtered. The filtrate was evaporated on a rotary evaporator under vacuum at room temperature to dryness to obtain the product (320 mg, 67% yield) as a colorless liquid. $^1$H-NMR (acetone-$d_6$): 13.03 (br S); $^{13}$C-NMR (acetone-$d_6$): 123.74, 145.38 and 158.719 (t).

The product obtained above, i.e. 3-chlorocarbohydroxymoyl-4-nitro-1,2,5-oxadiazole, was used in the next step without any further purification. The nitro compound (320 mg) was dissolved in diethyl ether (5 ml). To this solution was added at room temperature drop-wise a solution of potassium carbonate (166 mg) in water (3 mL). The reaction mixture was then stirred at room temperature for 2 h. Ether layer was separated and the aqueous layer was extracted with diethylether (2×5 mL). The combined organic layer was then washed with water (1×5 mL), brine (1×5 mL), dried ($Na_2SO_4$) and filtered. The organic solution was evaporated under vacuum at room temperature on a rotary evaporator. The pale yellow crude solid residue thus obtained was triturated with ether (1 mL). The white solid was separated via filtration and air dried. Yield: 68 mg (27% from nitro derivative) m.p.: 107-108° C. (Lit m.p. 108-110° C.).[1a] $^{13}$C-NMR (acetone-$d_6$): 104.45, 138.20, 140.55, 143.83, 160.82 (2 C).

While embodiments have been set forth as illustrated and described above, it is recognized that numerous variations may be made with respect to relative amounts of the constituents in the composition. Therefore, while the invention has been disclosed herein, it will be obvious to those skilled in the art that additions, deletions and modifications can be made without departing from the spirit and scope of this invention, and no undue limits should be imposed, except as to those set forth in the following claims.

What is claimed is:

1. The process for preparing 3-chlorohydroximoyl-4-nitro-1,2,5-oxadiazole comprising the steps of:
   (a) reacting 4-amino-3-chlorocarbohydroxymoyl-1,2,5-oxadiazole in the presence of a tungsten based catalyst and aqueous $H_2O_2$;
   (b) heating the solution at greater than 30° C. to produce 3-amino-4-chlorohydroximoyl 1-2,4-oxadiazole in solution;
   (c) isolating the 3-chlorohydroximoyl-4-nitro-1,2,5-oxadiazole from the solution.

2. The process of claim 1 wherein the tungsten based catalyst is $(Bmim)_4W_{10}O_{23}$.

3. The compound, 3-chlorohydroximoyl-4-nitro-1,2,5-oxadiazole, prepared according to the process of claim 1.

4. A process for preparing 3,4-Bis(4-nitro-1,2,5-oxadiazol-3-yl)-1,2,5-oxadiazole-N-oxide (DNTF) comprising:
   (a) dissolving 3-chlorohydroximoyl-4-nitro-1,2,5-oxadiazole prepared according to the process of claim 1 in diethyl ether;
   (b) adding drop-wise a solution of potassium carbonate;
   (c) stirring the mixture;
   (d) isolating the DNTF from the organic layer.

* * * * *